(12) United States Patent
Ferrand

(10) Patent No.: US 6,334,262 B1
(45) Date of Patent: Jan. 1, 2002

(54) GAUGE AND METHOD FOR MEASURING ANIMAL BACKS AND SADDLES

(76) Inventor: Robert J. Ferrand, 121 Bancroft Rd., Burlingame, CA (US) 94010

( * ) Notice: Subject to any disclaimer, the term of this patent is extended or adjusted under 35 U.S.C. 154(b) by 0 days.

(21) Appl. No.: 09/062,982

(22) Filed: Jul. 31, 2000

Related U.S. Application Data

(60) Provisional application No. 60/044,526, filed on Apr. 22, 1997.

(51) Int. Cl.$^7$ .................................................. G01B 3/14
(52) U.S. Cl. ......................... 33/511; 33/561.3; 33/452; 119/174; 54/1
(58) Field of Search ........................... 33/511, 501, 512, 33/514.2, 516, 545, 546, 561.1, 561.2, 561.3, 562, 1 BB, 452, 456, 481; 600/594; 119/174; 54/1

(56) References Cited

U.S. PATENT DOCUMENTS

| | | | | |
|---|---|---|---|---|
| 365,873 A | * | 7/1887 | Spence | 33/514.2 |
| 742,937 A | * | 11/1903 | Way | 33/514.2 |
| 889,224 A | * | 6/1908 | Haas | 33/514.2 |
| 1,129,081 A | * | 2/1915 | Edmonds | 33/561.2 |
| 1,234,527 A | * | 7/1917 | Berriman | 33/512 |
| 1,268,002 A | * | 5/1918 | Goodwin | 33/561.2 |
| 3,964,169 A | * | 6/1976 | Bush | 33/511 |
| 5,375,397 A | | 12/1994 | Ferrand | |

OTHER PUBLICATIONS

Harman, Joyce, Practical use of Computerize Saddle Pressure Measuring Device to Determine the Effects of Saddle Pads in the Horse's Back, 1994.

* cited by examiner

Primary Examiner—Andrew H. Hirshfeld

(57) ABSTRACT

This invention is a simple device and method of measurement that employs a mechanical device having articulated transverse linkages comprising a parallelogram assembly having the first arm as one link, an opposing link, and further comprising a hub member, with transverse opposing wings each of the wings being pivotingly joined to the hub member for defining shape and indicia to determine a series of angles, and thereby be able to describe angles and arcs in order to determine the convex and concave portions of polyform shapes—in this preferred embodiment relating to animal backs and their corresponding saddles. A method and formula to adjust the shape of such a device to compensate for the weight of the rider relative to the weight of the animal as well as additional factors is also provided by this process. Additional calibration can also be refined by employing interface pressure measurement.

19 Claims, 3 Drawing Sheets

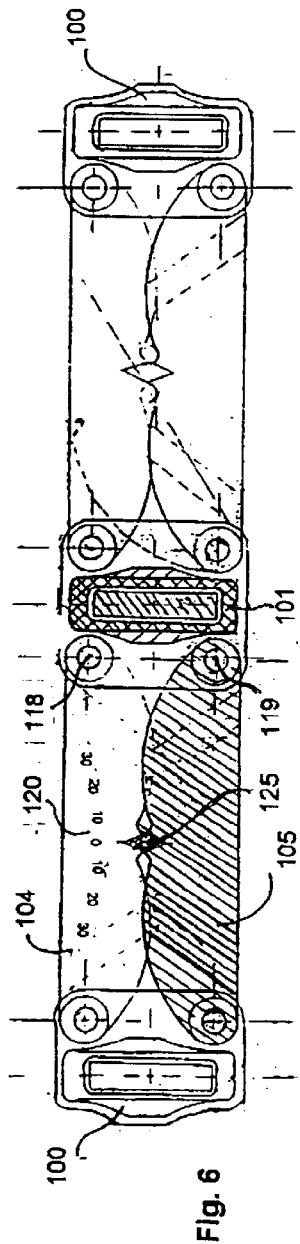
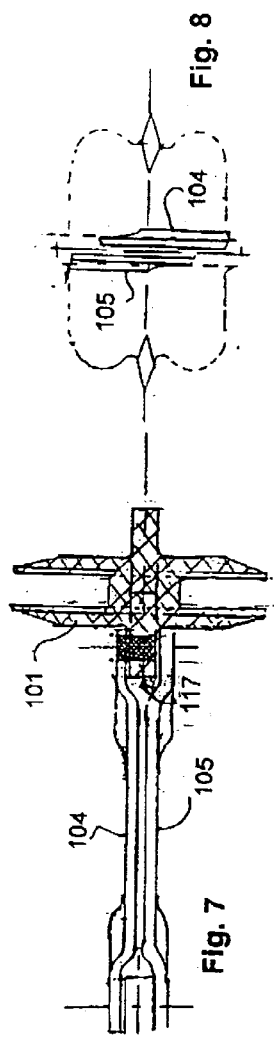
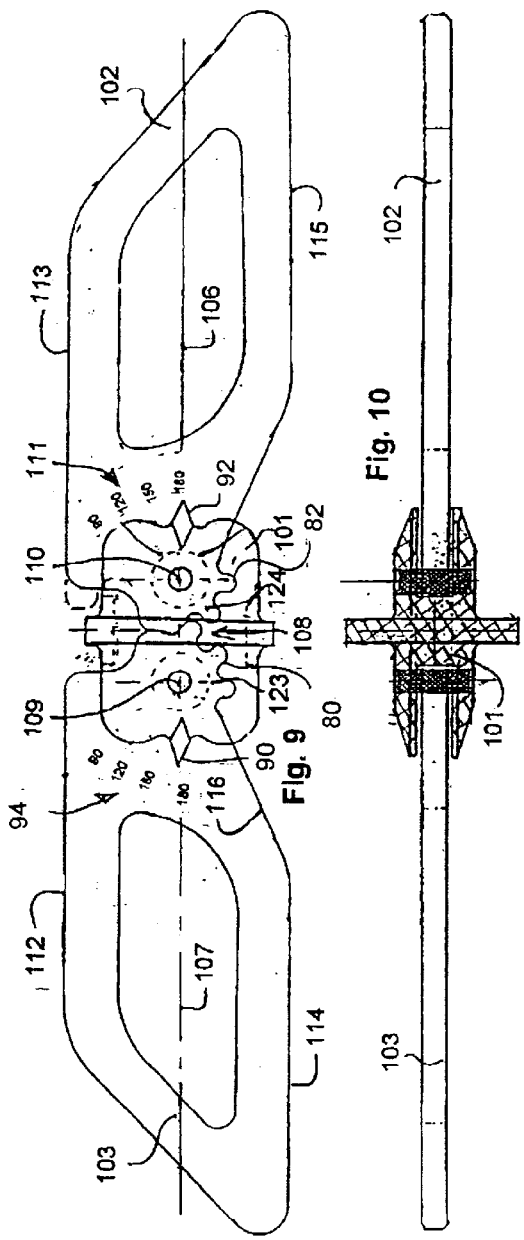

GAUGE AND METHOD FOR MEASURING ANIMAL BACKS AND SADDLES

CROSS-REFERENCE TO RELATED APPLICATION

This application claims the benefit of U.S. Provisional Application No. 60/044,526 filed Apr. 22, 1997.

BACKGROUND OF INVENTION

1. Field of Invention

This invention relates to the measurement of the compound curved surfaces of animal backs and the corresponding surfaces of saddles. In particular, this invention is directed to a device having articulated transverse linkages for defining the compound curved surface of animal backs and saddles with numerical values. This invention includes a formula to determine the amount of deflection of the animal's back caused by the weight of the rider so that that the correct fit of the saddle can be determined. Employing the preferred method of measurement the formula can be adjusted to compensate for additional factors such as breed, age or conditioning by employing interface pressure measurement.

2. Related Art

For centuries, people have ridden animals with a multitude of different saddles, but with very little scientific understanding of the effect of the saddle on the animal. The issue of saddle fit is not only important in the context of the humane treatment of the animal, but has even greater importance to equestrians who participate in sports that demand greater athletic performance from the animal. Signs of saddle related trauma include behavior problems, tenderness, loss of hair, white hairs, open sores, and certain forms of lameness.

Current methods of saddle fitting include using baling wire, flexible curves, cardboard templates, and plaster casts. The most sophisticated device is a pegboard. This centuries old device is comprised of a flat board with usually about one hundred holes through which dowels are fitted. By placing this device on the animal's back and adjusting the individual dowels so that they each just touch the surface of the animal a mirror image of the shape of the animal's back can be duplicated.

The disadvantage to the pegboard device and all other methods currently employed is that the effect of the weight of the rider is not considered. While the current commercial understanding of saddle fit assumes that the shape of the mirror image of the animal's back is the preferred saddle fit, objective pressure measurement has proven this not to be true. By employing U.S. Pat. No. 5,375,379 A Curve Conforming Sensor Array and Method for Measuring Pressures between a Saddle and a Horse it has been revealed that the weight of the rider causes sufficient deflection to the animal's back to cause the saddle not to fit. The reason for this is that the animal's back sags a little bit under the additional rider weight, which is significant enough to cause "bridging" meaning that the saddle only touches on the wither and the loin of the animal, causing trauma to the animal.

A more significant disadvantage to all prior devices and methods to fit saddles is that these devices and methods do not provide any numerical or calibrated measurement. Without numerical values the error in these devices cannot be determined or corrected.

Prior to 1993, there had never been an objective method to determine saddle fit. U.S. Pat. No. 5,375,379. This interface pressure measurement device can be used to adjust the saddle to the animal by trial and error, however; this is not practical in general commerce. Another disadvantage to this sensor array is that it does not provide the three-dimensional coordinates required to relate the shape of the saddle to the shape of the animal's back, so the correct saddle can be chosen or adjusted to fit the animal.

However, by employing this interface pressure measurement device in conjunction with a three dimensional measurement gauge made according to the invention, the amount of deflection in the animal's spine caused by the weight of the rider can be determined and reduced a formula and the formula can be adjusted to compensate for additional factors, such breed, age or conditioning by employing interface pressure measurement.

SUMMARY OF INVENTION

This disclosure describes a Gauge and Method for measuring animal backs and saddles in order to provide objective numerical values to determine saddle fit. By application of this preferred embodiment of this device and this method of measurement the compound curved surface of animal backs and their corresponding saddles can be determined.

The present invention overcomes the limitation of previous known prior art. In particular, this invention permits a series of numbers to define the twist and arc which comprise the compound curved surface of animal backs and their corresponding saddles as well as a formula to compensate for the deflection in the animal's back caused by the weight of the rider. Employing the preferred method of measurement additional factors such as breed, age or conditioning can also be compensated by employing interface pressure measurement.

In general, by using the calibrated measurements from this Gauge, the incremental effect of the weight of the rider on the animal's back can be approximated to determine a more accurate size and shape of saddle for a particular animal and rider combination. The age of the animal, the style of riding, the type of saddle and the conditioning of the animal will also affect this calculation. By using the calibrated measurements a variety of interrelationships can be easily calculated to determine a superior fitting saddle.

To verify that these calculations are in fact accurate or to refine the rider and animal weight compensation formulas, we must use the Curve Conforming Sensor Array and Method for Measuring Pressures between a Saddle and a Horse disclosed in U.S. Pat. No. 5,375,379.

This technology consists of a pressure sensitive pad attached to a computer. The pad contains an array of 256 pressure sensors that measures 24 inches by 32 inches. To use this pressure sensitive pad, the pad is placed between the animal and the saddlelpad combination and is connected to the computer. When the rider mounts the animal, the system graphically displays a variable color map that shows the amount of pressure and the location of the pressure exerted by the saddle and rider on the animal.

If the Gauge or the computer scan reveals that the saddle is "bridging," causing high pressure on the withers and loin, the measurement of the arc of the saddle can be increased incrementally to permit the saddle to contact the back of the animal and evenly distribute the weight over the entire saddle panel. Conversely, if the gauge or the computer scan reveals that the saddle "rocks," causing high pressure only on the middle of the back of the animal (no contact on the withers or loin), the arc of the saddle can be decreased to permit the saddle to contact the back of the animal and evenly distribute the weight over the entire saddle panel.

This invention is generally directed to a gauge for measuring the curvature of the back of an animal along transverse directions comprising first, second, third and fourth elongate arms. The first and second elongate arms extend in a line and have ends joined for pivoting about a first axis transverse to the line. The third elongate arm extends transverse to the first line and is mounted relative to the first and second arms for pivoting about a second axis transverse to the first axis. The fourth arm also extends transverse to the line and is mounted relative to the first and second arms for pivoting about a third axis also transverse to the first axis. The gauge is positionable on the back of an animal with the first and second arms aligned along the spine and each arm in contact with the surface of the back of the animal.

A preferred gauge and method of measurement according to the invention employs a mechanical device having articulated transverse linkages comprising a parallelogram assembly having the first arm as one link, an opposing link, and further comprising a hub member, with transverse opposing arms or wings, each of the wings being pivotingly joined to the hub member for defining shape and indicia to determine a series of angles, and thereby be able to describe angles and arcs in order to determine the convex and concave portions of polyform shapes—in this preferred embodiment relating to animal backs and their corresponding saddles. A method and formula to adjust the shape of the device to compensate for the weight of the rider relative to the weight of the animal as well as additional factors is also provided by this process.

The preferred embodiment is a gauge for measuring the curvature of the back of an animal along transverse directions comprising: sets of arms or wings that extending in a line which joined for pivoting about a first axis transverse to the line; and a third arm extending transverse to the line, and mounted relative to the first and second arms for pivoting about a second axis transverse to the first axis, the gauge being positionable on the back of the animal with at least one link aligned along the spine and each transverse arm or wing in contact with the surface of the animal.

Additionally, a method of measuring a saddle to the back of an animal using at least one gauge having a plurality of relatively articulating spine segments and a plurality of pairs of opposing arms or wings extending transversely at spaced locations along the spine segments and articulating transverse to the spine segments, comprising the steps of: positioning such a gauge over the back of an animal with each of the plurality of spine segments aligned over the spine of the animal.

While maintaining the alignment of the spine segments over the back of the animal, positioning each of the wings in contact with the back of the animal, the points of contact of the wings defining a spacial array of points of the surface of the back of the animal positioning such a gauge so that the spine segments are positioned substantially the same as the spine segments of the a gauge positioned over the back of the animal and the wings are positioned to provide an array of points which conform spacially to the array of points in contact of the wings with the back of the animal and which are opposing in position relative to the surface defined by the back of the animal; and while maintaining the relative positions of the spine segments and the wings in the opposite position, positioning the gauge against the surface of the saddle which faces the animal during use, and determining where the saddle contacts or does not contact the wings at the array of points.

These and other features and advantages of the present invention will be apparent for the preferred embodiment described in the following detailed description and illustrated in the accompanying drawings.

DESCRIPTION OF THE SEVERAL VIEWS OF THE DRAWINGS

FIG. 6. is a side view of a three-wing section gauge made according to the invention.

FIG. 7. is a top view of a hub section and linking means used in the gauges of FIGS. 1, 5 and 6.

FIG. 8. is an end view of the hub section and linking means of FIG. 7.

FIG. 9. is a front view of the hub section and left and right wings of the gauges of FIGS. 1, 5 and 6.

FIG. 10. is a top view of the hub section and left and right wings of FIG. 9.

DETAILED DESCRIPTION OF THE PREFERRED EMBODIMENTS

Figure 1:
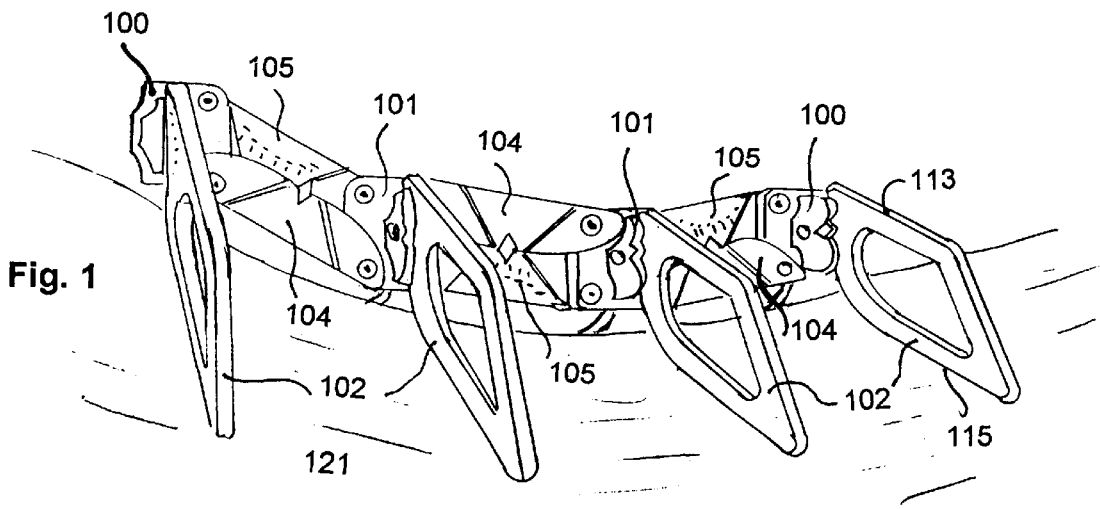
FIG. 1. is a side oblique view of a four-wing gauge made according to the invention on the back of an animal.

As has been mentioned, this invention is a simple device and method of measurement that employs a mechanical device having, in its preferred forms, articulated transverse linkages comprising a parallelogram assembly having the first arm as one link, an opposing link, and further comprising a hub member, with transverse opposing wings each of the wings being pivotingly joined to the hub member for defining shape and indicia to determine a series of angles, and thereby be able to describe angles and arcs in order to determine the convex and concave portions of polyform shapes—in this preferred embodiment relating to animal backs and their corresponding saddles. A method and formula to adjust the shape of such a device to compensate for additional factors is also provided by this process.

A saddle generally only contacts the animal on two areas which rest on either side parallel to the spine at the distance of about two inches and are generally 6 inches wide by 20 inches long. While the animal's body is generally round, the back of the animal in contact with the saddle is actually relatively flat. This anatomical feature permits this invention to have greater accuracy.

The preferred embodiment of this invention will permit measurement of a polyform shape by breaking this complex shape into a series of short lines. By describing the interrelationship of these lines to each other, a complex polyform shape can be determined. The preferred embodiment of this invention permits a simple easy device and method to determine those interrelationships.

Referring initially to FIG. 9, by using a series of opposing wings 102 and 103 having respective centers of rotation 109 and 110 relative to a hub are spaced apart but geared to each other in region 108 by respective intermeshed gears 80 and 82. The angle of two opposing pad areas are measured in relationship to each other by the position of oppositely directed respective pointers 94 and 92 fixed to a hub 101 relative to associated respective indicia 90 and 111. Due to the intermeshing of gears 80 and 82, the two pairs of pointers and associated indicia are redundant in that they both indicate the same angle. Accordingly, in this embodiment only one of the pointers and associated indicia is required. In an alternative embodiment, the wings are not connected by intermeshed gears and are accordingly independently pivotable about axes 109 and 110. The relative angle between the two wings is then the sum of the angle of each relative to hub 101.

Figure 2:
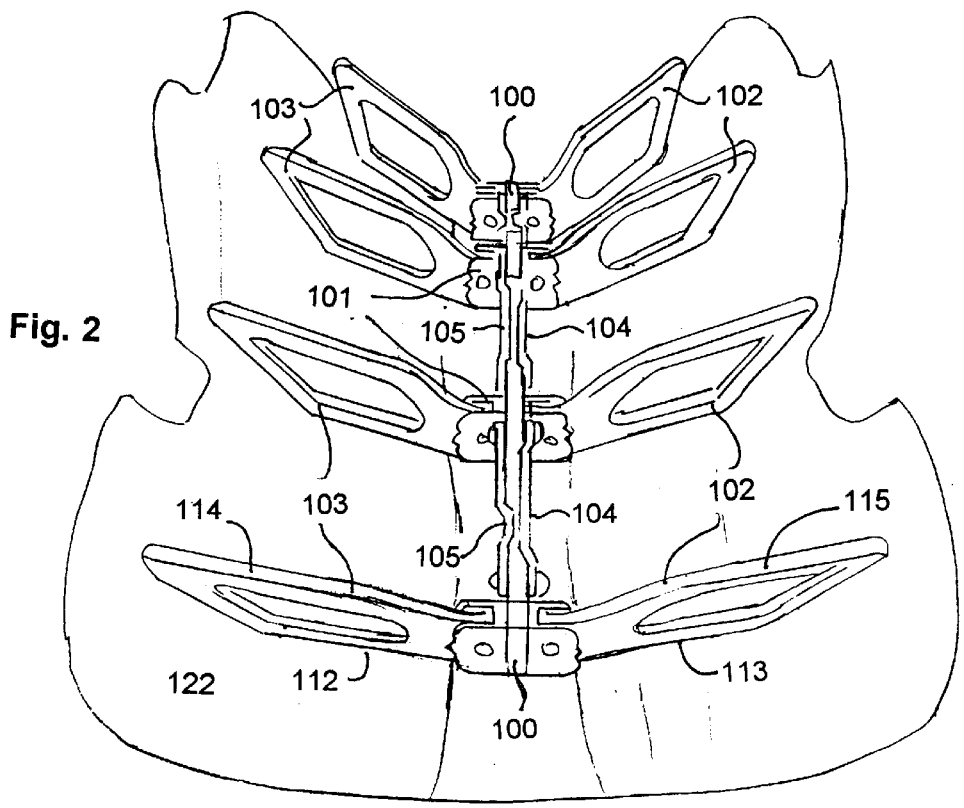
FIG. 2. is a top oblique view of the four-wing gauge of FIG. 1 in a saddle.
Figure 3:
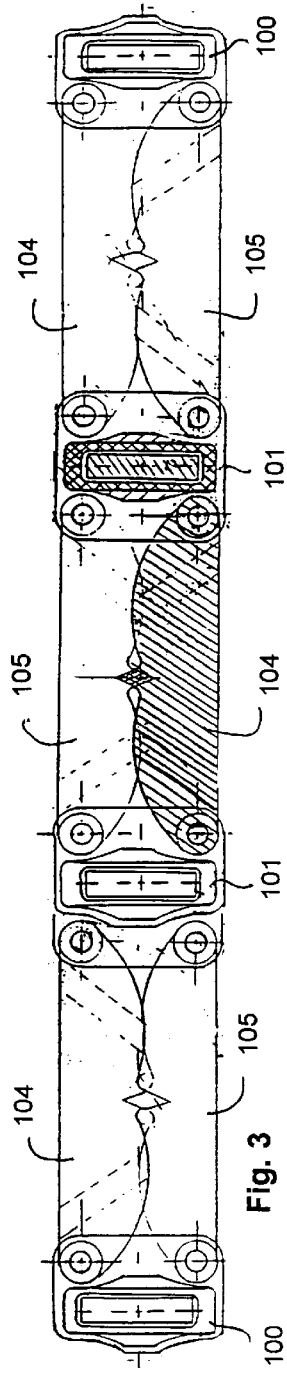
FIG. 3. is a side view of the four-wing section gauge of FIG. 1 with the central links positioned along a horizontal line.

By making the wing equidistant in height along the axis (FIG. 9 #106 & #107) two measurements can be made by one device. Using the top surface (FIG. 9 #112 & #113) to measure the saddle (FIG. 2 #122) and the bottom surface (FIG. 9 #114 & #115) to measure the animal (FIG. 1 #121). If the wing is tapered on the bottom toward the inside end to clear the spine of the animal (FIG. 9 #116), the angle of the animal's back can be measured (FIG. 1 #115). The measurement of the angle inside the saddle can also be measured by turning the device upside down and using the other side for the corresponding measurement (FIG. 2 #112 & #113).

This section of the preferred embodiment of this device consists of basically two parts, a hub (FIG. 9 #101) and a wing (FIG. 9 #102). A third part is the same wing section, FIG. 9 #103 with the only difference being that the geared section of one of the wings (FIG. 9 #123) is offset to mate (FIG. 9 #108) with the opposing gear of the opposing wing (FIG. 9 #124). This section can measure angles from 60 degrees to 180 degrees (FIG. 9 #111). While the lower section of the device could measure angles less than 90 degrees, the measurements of the saddle using the upper side of the unit would begin to not correspond to the lower section once the upper section toggles when adjusted beyond the 90 degree point, thus additional compensation is required. This feature is of benefit because the saddle pad becomes a significant factor in the measurement. Employing this feature and additional compensation a superior measurement is achieved.

Any number of the these angle measurement sections can be linked together using two links (FIG. 6 #104 & #105), (FIG. 6) has three wings, (FIG. 4) has 4 wings and (FIG. 5) has five wings. These two links (FIG. 6 #104 & #105) attach in a perpendicular fashion to the wing sections at the hub on a flange (FIG. 7 #117). Each link attaches on opposite sides of the hub flange, (FIG. 8 #104 & #105). One links the two top parts of the two adjacent flanges FIG. 6 #118) and the second link attaches to the bottom side of the same two adjacent flanges (FIG. 6 #119).

Figure 4:
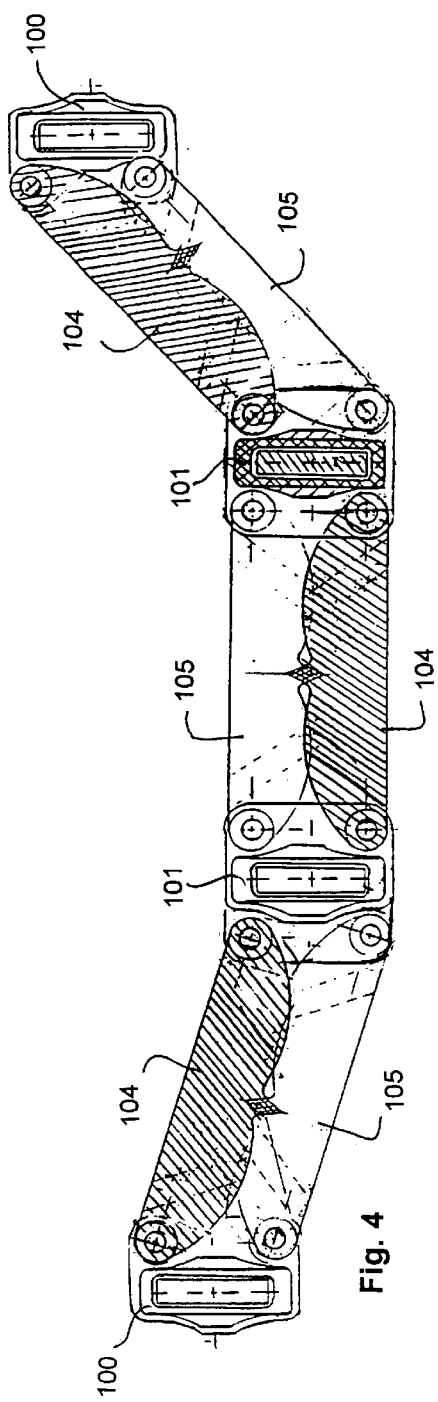
FIG. 4. is a side view of the four-wing section gauge of FIG. 1 showing articulation of two opposing links and corresponding hubs.

The series of links permit the relationship of the individual wing angle measurements to be measured in relationship to each other (FIG. 6). By creating a parallelogram using the opposing flange edges and with the links attached top and bottom, each of the wing sections will remain parallel to each other as one is moved upward relative to the other, as shown in FIG. 4. Since this device is measuring a series of angles, if each of the angles are not maintained parallel to each other the accuracy of the device is compromised. Thereby, arcs can be determined by segmenting the arc into a series of angles Since a polyform shape is both a series of angles and a series of arcs, by measuring the angle of two parallel angle interrelationships an ARC can be determined. The larger the number of wings that measure the arc the greater the accuracy of the measurement of that arc. Three wing sections (FIG. 6) are the minimum necessary to determine an arc with one device and five wing sections (FIG. 5), is the most accurate number. Additional wings can be added but the number of measurements becomes difficult to manage after five wings.

Figure 5:
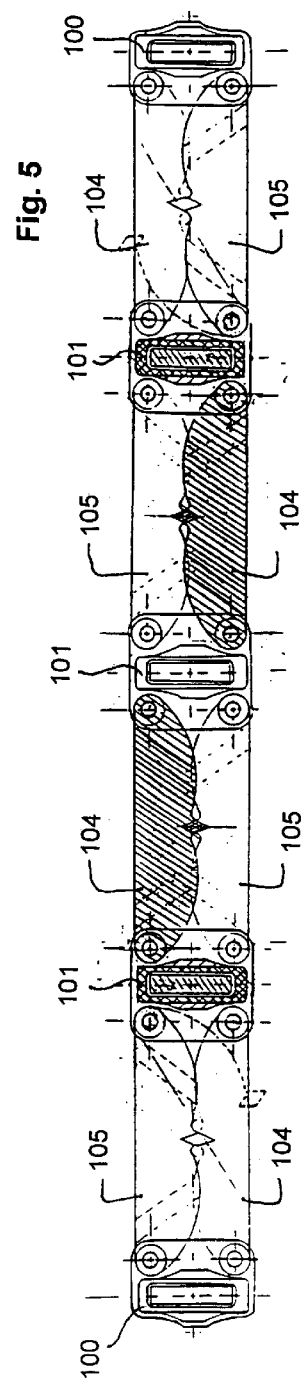
FIG. 5. is a side view of a five-wing section gauge made according to the invention.

It is important to note that the relationship between the top polyform shape and the bottom polyform shape is not a linear relationship, exactly a one to one relationship. While the wing angles do maintain a linear relationship the interrelationship of the top and bottom arcs does have some hysterisis and is not constant throughout the scale. In order to maintain each of the wing section faces parallel to each other a parallelogram has been employed (FIG. 6). The parallelogram does rotate about an axis of rotation toward the center of the corresponding hub. This rotation does cause the upper section arc to be slightly less than the corresponding lower section arc causing the upper side to be slightly more concave than the lower convex section. It is important to note that the smaller the number of wings section, the more pronounced this hysterisis will be. Thus a three-wing unit (FIG. 6) has more hysterisis than a fivewing device (FIG. 5).

This unique feature is actually an advantage in fitting saddles. One of the most difficult aspects to determining saddle fit is determining the arc of the back, because once the rider mounts the animal, the leather covering the sides of the saddle prevents anyone from actually observing how the panels of the saddle contact the animal. The arc measurement is a unique feature to this device permitting the device to automatically put a little bit of additional arc to the saddle measurement to compensate for an average rider's weight, due to the hysterisis in the gauge itself.

Traditionally saddles are fit to unloaded animals because one can lift the flap of the saddle and look at how the saddle rests on the animal. The problem arises when the rider mounts, because the spine of the animal deflects (curves) downward relative to the weight of the rider. While a variety of other factors do have influence, such as the condition of the animal, the style of the riding and the skill of the rider, generally if the saddle fits the unloaded animal, the saddle can increasingly bridge (touching the withers and loin only) once the rider mounts into the saddle.

The principle is simple; for example, a large draft animal of 1500 pounds will not be greatly affected by the weight of a 100-pound rider because the rider represents about 6.5% of the animal's weight. By contrast, a 250-pound rider on a 1000-pound animal would represent 25% of the animal's weight. One animal has a force representing 6.5% the other 25% acting upon them, obviously these would have different effects on the curvature of the different animal backs.

Another important feature of the preferred embodiment of this device is calibration. By adding numerical calibration this device substantially increases its utility. By physically measuring the angle between the wing sections of the device a series of numbers can be scribed on the wing (FIG. 9 #111) in relationship to a common point on either side of the hub section. In a totally different method, a fixed point (FIG. 6 #125) can be made on the inner face of the link section. As the angle of the device changes, the relationship of the two links, (FIG. 6 #104 & 105), to each other will change proportionately. By calibrating this interrelationship to known angular measurements (FIG. 6 #120) a new interrelationship creating an arc can be established.

These numerical calibrations permit a variety of advantages. First, a measurement can be taken and then recorded. At a later date the same series of numbers can be used to readjust the Gauge and thereby be able to duplicate a polyform shape at a different time and place. A practical use of this feature would permit the measurement of an animal in California. The series of numbers could then be sent to another country to a saddler with a corresponding Gauge and a saddle could be adjusted to those measurements using the same polyform shape for an animal that is thousands of miles away.

This numerical system also permits an equestrian to measure the animal and then go from saddle shop to saddle shop to find a saddle with corresponding measurements. The same tool can also be used by a saddlemaker to readjust existing saddles. The saddler can use the device as an adjustable template while the saddle is in the shop for adjustments, thereby eliminating the trial and error method that is currently employed. Over time if the measurements are recorded and the response of the animal is noted—objective correlation can be made to subjective observations.

The most important aspect of calibrated measurement is permitting a method to compensate for the weight of the rider in relationship to the weight of the animal. Until the development of this device there has been no method to estimate the effect of the weight of the rider relative to weight of the animal.

The preferred embodiment of this invention permits a method to determine a formula that can use the measurement from an unloaded animal to approximate the effect of the load of the saddle and rider on the animal. By adding a calculated number of degrees (A), corresponding to the angle of adjustment of one degree, for each increment of rider weight (B) greater than an established rider weight (C), relative to the rider's weight (RW) the curvature of the gauge can be increased to approximate the curvature the spine of the animal would experience placed under that incremental higher rider weight. Conversely, the formula can be reversed for a lighter rider with weight less than a known established rider weight which would have less effect on the animal and the arc could be proportionately reduced.

The same principle also affects the weight of the animal. By subtracting a calculated number of degrees (X), corresponding to the angle of adjustment of one degree, for each increment of animal weight (Y) greater than an established animal weight (Z), relative to the animal's weight (AW) the curvature of the gauge can be decreased. Conversely, if the weight of the animal is less than an established animal weight it would be affected more by the weight of the rider and should therefore have a calculated number of degrees added to the arc of the gauge and the saddle.

By testing in the field, the accuracy of the formula as well as, the established rider weight (C), the incremental rider weight (B), the established animal weight (Z), the incremental animal weight (Y), can be determined by the use of an interface pressure measurement device. By correlating the shape of the gauge, determined by indicia, with the measurement of the actual pressure exerted on the saddle, a mathematical relationship can be determined. By using the real numbers of the animal weight and rider weight and then experimenting with the other factors (C, B, Z, Y) by trial and error; a set of numbers that equate to a saddle that creates even pressure on the animal's back can be determined for a number of animals. Once the established rider weight (C), the incremental rider weight (B), the established animal weight (Z), the incremental animal weight (Y) are established; additional factors such as age, breeding and conditioning can be determined by the deviation from these numbers. This method creates a feedback loop that corrects for the hysterisis in the gauge itself as well as a variety of other factors, which increases accuracy.

The basic formula for a four wing gauge to compensate for rider weight is $A=(RW-C)/B$. In this formula, A is a change in angular position of a wing, RW is the weight of the rider, C is the established standard rider weight, and B is an established weight corresponding to a one degree change in angular position of the wing. In a typical example, the value of C is 150 lbs., and the value of B is 15 lbs. The basic formula to compensate for animal weight is $X=(Z-AW)/Y$ where X is a change in angular position of a wing, Z is the established standard animal weight, AW is the weight of the animal, and Y is an established weight corresponding to a one degree change in angular position of the wing. In a typical example, the value of Y is 100 lbs., and the value of Z is 1000 lbs. By adding the two factors together a weight compensation factor, $WCF=A+X$, can be determined. The wither and loin arcs can then be adjusted accordingly and the shape of the mounted animal's back is thereby determined.

It is important to note that the formula that is appropriate for the 4-wing gauge is different than the formula for the 5-wing gauge. This is due to a number of factors. First the 5-wing gauge is larger and therefore is measuring over a greater area and the incremental hysterisis between the top and the bottom of the gauge is not the same. Second the actual surface area that the 5 wing gauge measures is actually 25% more than the 4-wing gauge and will thus have less effect on the animal. This means that the same load is spread over a larger area and will not have the same effect as is measured by the 4-wing gauge.

The basic formula for a five wing gauge to compensate for rider weight is $A=(RW-C)/B$. In a typical example, the value of C is 100 lbs., and the value of B is 25 lbs. The basic formula to compensate for animal weight is $X=(Z-AW)/Y$, wherein example values of Y and Z could be 100 lbs. and 1000 lbs., respectively. By adding the two factors together a weight compensation factor, $WCF=A+X$ can be determined. The wither and loin arcs can then be adjusted accordingly and the shape of the mounted animal's back is thereby determined. wherein example values of Y and Z could be 100 lbs. and 1000 lbs., respectively. Numerical values do permit formulas to compensate for a variety of factors. By adjusting the calculated number of degrees (X) or (A) by changing the incremental animal weight (Y) or the incremental rider weight (B) or the established animal weight (Z) or the established rider weight (C) the curvature of the arc of the gauge can be adjusted for a variety of factors.

Additional data acquired from the computer saddle fitting system can be used to refine the formulas to compensate for additional factors and increase the accuracy of the formulas. By testing a variety of animals under various loaded conditions a relationship between the Gauge measurements and actual real time interface pressure measurements can be made using the interface pressure measurement device (U.S. Pat. No. 5,375,379) to develop a data base and offset table and thereby compensate for the hysterisis in the gauge as well as the variety of factors affecting the animal.

Since saddle fit is affected by a variety of factors, including the weight of the rider, the weight of the animal, the age of the animal, the condition of the animal, the type of saddle, the surface area of the saddle panels, the type of riding and the skill of the rider, a variety of adjustments to this formula will evolve over time using this instrument. It is anticipated that groups will begin to develop schools of thought to interpret the formula in different ways as well as establish new formulas and standards for particular styles of riding and riding disciplines.

A subtle variation of this measurement is also provided by this invention. Many animals are not even side-to-side. The preferred embodiment permits a few degrees of variation to be measured side to side. Lifting one wing upward while holding the opposite wing down will permit this measurement. This is accomplished by adjusting the backlash in the gears to a fraction of an inch, but just enough so that when the wings are moved simultaneously they measure symmetrically. However by forcing the wings in opposite directions an asymmetrical measurement can be observed.

The preferred method to measure an animal would be:

1. Be sure that the animal is standing with all four feet square to each other and that the animal's head is in a normal position when riding.
2. Place the Saddle on the animal
3. Adjust the wings to 120 degrees and the wither and loin arc to 25 degrees. The purpose of this adjustment is to put the Gauge in a configuration only to facilitate ease of measurement so that the wings would be nearer the adjusted angle and the wither and loin wings are out of the way for initial placement.
4. Center the Gauge on the animal in the same position that you will put the center of the saddle, meaning centered between the previously marked position of the saddle. Make sure that the wings are adjusted perpendicular to the ground.
5. Adjust the Center wings down so that the bottom edges of the wings have maximum contact with the animal's back.
6. Adjust the wither and loin wings down so that the bottom edges have maximum contact with the animal's back.
7. Double Check that the faces of the Wings are perpendicular to the ground.
8. Record the Measurements from each of the respective wing (arm) indicia and the arc (link) indicia on the Gauge and Photograph the Gauge on the animal The following is an example of the measurements from a four-wing gauge.

|  | Wither | Shoulder | Center | Back | Loin |  |
| --- | --- | --- | --- | --- | --- | --- |
| 90° Angle | [25°] Arc | 110° Angle | [0°] Arc | 120° Angle | [15°] Arc | 140° Angle |

(Note that devices with a greater number of wings will also have a proportionately larger number of measurements and vise versa.)

The preferred method to measure the Saddle would be:

9. Lift the Gauge off the animal without moving the position of the Gauge.
10. If necessary, adjust wither ((pommel) arc and loin (cantle) arcs of the Gauge using the WCF (Weight Compensation Factor) to compensate for the weight of the rider relative to the weight of the animal using the appropriate formula.

The relative angle of the wings to each other are varied an amount determined by the equation $WCF=(RW-C)/B+(Z-AW)/Y$, where WCF is the change in the angle of the wings to each other, by adjusting the wither and loin arcs by that amount. RW is the weight of the rider, C is the established weight of the rider, B is the variance in weight of the rider from the established weight of the rider corresponding to the angle of adjustment of one degree, AW is the weight of the animal, Z is the established weight of the animal, and Y is the variance in the weight of an animal from the established weight of the animal corresponding to an angle of adjustment of one degree.

Note: additional factors may require refined formulas. Additional factors affecting saddle fit include the age of the animal, the condition of the animal, the type of saddle, the surface area of the saddle panels, the type of riding and the skill of the rider. Appropriate adjustments can be made using this method to account for additional factors.

11. Turn the Gauge upside down and place the Gauge in the Saddle.
12. Center the Gauge in the center of the saddle, equidistant from the front (pommel or fork) and back (cantle) of the saddle.
13. Determine the best possible saddle fit for a particular animal.

The saddle "Fits": if all the wings touch the saddle uniformly.

The saddle "Rocks": if the wither and loin wings touch the saddle only in the center and are a distance from the saddle at the wither and loin.

The saddle "Bridges": if all the wither and loin wings touch the saddle at the pommel (front) and cantle (back) and do not touch in the center of the saddle.

14. By making an additional measurement employing an interface pressure measurement device, the formula can be calibrated to adjust for additional factors such and age, breeding, or conditioning.

If the gauge or computer scan reveals that the saddle is "bridging," causing high pressure on the withers and loin, the measurement of the arc of the saddle can be increased incrementally to permit the saddle to contact the back of the animal and evenly distribute the weight over the entire saddle panel by adjusting incremental rider weight (B) or the incremental animal weight (Y) Conversely, if the gauge or the computer scan reveals that the saddle "rocks," causing high pressure only on the middle of the back of the animal (no contact on the withers or loin), the arc of the saddle can be decreased to permit the saddle to contact the back of the animal and evenly distribute the weight over the entire saddle panel, by adjusting either the established rider weight (C) or the established animal weight (Z), Using the preferred embodiment of this invention and the preferred method of measurement a variety of differently shaped animal backs can be measured. The same instrument can also be used to determine if a particular saddle can be fit to a particular animal.

Variations to this invention are possible using different mechanical means. The wings can be suspended inside of a tube using washers with incline planes that function as wedges to lock the position of the wings. That same tube can then become the rotational axis and bearing surface for links that would have holes at each end to receive the tube and similar washers with incline planes that would wedge the parts together and lock the system. This system would not be preferred because of the additional cost due to the greater of number of parts and the complexity of making such parts. The preferred invention uses a minimal number of parts for ease of manufacture. The enclosed figures describe the preferred embodiment of this invention.

By use of this device and the application of this method of measurement the convex and concave portions of polyform shapes of an animal's back and the corresponding saddles can be determined in a simple, cost effective manner Although the present invention has been described in detail with reference to a particular preferred embodiment, persons possessing ordinary skill in the art to which this invention pertains will appreciate that various modification and enhancements may be made without departing for the spirit and scope of the claims as written and as judicially construed according to principles of law. The above disclosure is thus intended for purposes of illustration and not limitation.

The invention claimed is:

1. A gauge for measuring the curvature of the back of an animal along transverse directions, said gauge comprising:
   a first hub, a second hub, and a third hub;
   a first connection mechanism movably connecting said first hub to said second hub;
   a second connection mechanism movably connecting said second hub to said third hubs, wherein said first and second connection mechanisms extend in a line and each of said hubs are movable with respect to each other;
   a first wing pivotally attached to said first hub about an axis substantially parallel to said line, said first wing extending substantially perpendicularly to said line in a first direction away from said line;
   a second wing pivotally attached to said first hub about an axis substantially parallel to said line, said second wing extending substantially perpendicularly to said line and extending in a second direction away from said line, said second direction being substantially opposite to said first direction;
   a third wing pivotally attached to said second hub about an axis substantially parallel to said line, said third wing extending substantially perpendicularly to said line and extending in said first direction;
   a fourth wing pivotally attached to said second hub about an axis substantially parallel to said line, said fourth wing extending substantially perpendicularly to said line and extending in said second direction;
   a fifth wing pivotally attached to said third hub about an axis substantially parallel to said line, said fifth wing extending substantially perpendicularly to said line and extending in said first direction; and
   a sixth wing pivotally attached to said third hub about an axis substantially parallel to said line, said sixth wing extending substantially perpendicularly to said line and extending in said second direction;
   said connection mechanisms being alignable with the spine of said animal, and said wings being engageable with the back of said animal to conform said gauge to the shape of the back of said animal.

2. The gauge as in claim 1, further comprising:
   a fourth hub;
   a third connection mechanism movably connecting said third hub to said fourth hub, said third connection mechanism extending along said line;
   a seventh wing pivotally attached to said fourth hub about an axis substantially parallel to said line, said seventh wing extending substantially perpendicularly to said line and extending in said first direction; and
   a eighth wing pivotally attached to said fourth hub about an axis substantially parallel to said line, said eighth wing extending substantially perpendicularly to said line and extending in said second direction.

3. The gauge as in claim 1, wherein said first connection mechanism includes a first pair of links pivotally attached to said first and second hubs forming a first parallelogram assembly, and said second connection mechanism includes a second pair of links pivotally attached to said second and third hubs forming a second parallelogram assembly.

4. The gauge of claim 3, wherein said first and second pairs of links are each provided with indicia configured to indicate the extent of movement of said first pair of links relative to each other, and the extent of movement of said second pair of links relative to each other.

5. The gauge of claim 1, wherein each of said wings includes a first elongate edge for placement on the back of said animal and a second elongate edge spaced from, and parallel to, the first elongate edge thereof, the second edges defining a surface corresponding to the shape of the back of said animal when said gauge is placed on said back of said animal.

6. The gauge of claim 1, further comprising means for indicating the position of each wing relative to the hub to which it is attached.

7. A method of measuring the fit of a saddle to the back of an animal using a gauge, said gauge having a first hub, a second hub, and a third hub; a first connection mechanism movably connecting said first hub to said second hub; a second connection mechanism movably connecting said second hub to said third hubs, wherein said first and second connection mechanisms extend in a line and each of said hubs are movable with respect to each other; a first wing pivotally attached to said first hub about an axis substantially parallel to said line, said first wing extending substantially perpendicularly to said line in a first direction away from said line; a second wing pivotally attached to said first hub about an axis substantially parallel to said line, said second wing extending substantially perpendicularly to said line and extending in a second direction away from said line, said second direction being opposite to said first direction; a third wing pivotally attached to said second hub about an axis substantially parallel to said line, said third wing extending perpendicularly to said line and extending in said first direction; a fourth wing pivotally attached to said second hub about an axis substantially parallel to said line, said fourth wing extending substantially perpendicularly to said line and extending in said second direction; a fifth wing pivotally attached to said third hub about an axis substantially parallel to said line, said fifth wing extending substantially perpendicularly to said line and extending in said first direction; and a sixth wing pivotally attached to said third hub about an axis substantially parallel to said line, said sixth wing extending substantially perpendicularly to said line and extending in said second direction; said connection mechanisms being alignable with the spine of said animal, and said wings being engageable with the back of said animal to conform said gauge to the shape of the back of said animal, said method comprising:
   positioning the bottom side of said gauge onto the back of the animal, with said line positioned over the spine of the animal;
   positioning each of the wings in contact with the back of the animal, the points of contact between the wings and the back of the animal defining an array of points on the surface of the back of the animal;
   removing the gauge from the animal while maintaining the relative positions of the wings, connection mechanisms, and hubs;
   positioning the top side of said gauge onto the surface of the saddle that is to face said animal; and
   determining the locations where the saddle contacts said gauge.

8. The method of claim 7, wherein prior to the step of positioning the top side of said gauge onto the saddle, an angular position of at least one of said wings is adjusted in proportion to the difference between the weight of the animal and an established standard animal weight.

9. The method of claim 8, wherein said adjustment of the angular position of at least one of said wings is determined by the equation $X=(Z-AW)/Y$, where X is the change in angular position of the at least one wing, Z is the established standard animal weight, AW is the weight of the animal, and Y is an established weight corresponding to a one degree change in angular position of the at least one wing.

10. The method of claim 9, wherein Y is determined using an interface pressure measurement device for measuring pressure on the back of the animal.

11. The method of claim 9, wherein Z is determined using an interface pressure measurement device for measuring pressure on the back of the animal.

12. The method of claim 7, wherein prior to the step of positioning the top side of said gauge onto the saddle, an angular position of at least one of said wings is adjusted in proportion to the difference between the weight of the rider and an established standard rider weight.

13. The method of claim 12, wherein said adjustment of the angular position of at least one of said wings is determined by the equation $A=(RW-C)/B$, where A is the change in angular position of the at least one wing, RW is the weight of the rider, C is the established standard rider weight, and B is an established weight corresponding to a one degree change in angular position of the at least one wing.

14. The method of claim 13, wherein B is determined using an interface pressure measurement device for measuring pressure on the back of the animal.

15. The method of claim 13, wherein C is determined using an interface pressure measurement device for measuring pressure on the back of the animal.

16. The method of claim 7, wherein prior to the step of positioning the top side of said gauge onto the saddle, an angular position of at least one of said wings is adjusted in proportion to the difference between the weight of the animal and an established standard animal weight, and also in proportion to the difference between the weight of the rider and an established standard rider weight.

17. The method of claim 16, wherein said adjustment of the angular position of at least one of said wings is determined by the equation $WCF=(Z-AW)/Y+(RW-C)/B$, where WCF is the change in angular position of the at least one wing, Z is the established standard animal weight, AW is the weight of the animal, Y is a first established weight corresponding to a one degree change in angular position of the at least one wing, RW is the weight of the rider, C is the established standard rider weight, and B is a second established weight corresponding to a one degree change in angular position of the at least one wing.

18. The method of claim 17, wherein Y and B are determined using an interface pressure measurement device for measuring pressure on the back of the animal.

19. The method of claim 17, wherein Z and C are determined using an interface pressure measurement device for measuring pressure on the back of the animal.

* * * * *